(12) United States Patent
Gjertsen et al.

(10) Patent No.: US 10,688,260 B2
(45) Date of Patent: Jun. 23, 2020

(54) DEVICES AND SYSTEMS FOR AIR ASSISTED DRY POWDER ADMINISTRATION

(71) Applicants: MYSTIC PHARMACEUTICALS, INC., Austin, TX (US); Chris D. Shay, Horseshoe Bay, TX (US)

(72) Inventors: Jeffrey Gjertsen, Austin, TX (US); Phillip Goodman, Austin, TX (US); Jesse Hancock, Cedar Park, TX (US); Michael Shaw, Austin, TX (US); Timothy Sullivan, Austin, TX (US)

(73) Assignee: Mystic Pharmaceuticals, Inc., Austin, TX (US)

( * ) Notice: Subject to any disclaimer, the term of this patent is extended or adjusted under 35 U.S.C. 154(b) by 243 days.

(21) Appl. No.: 15/761,736

(22) PCT Filed: Sep. 26, 2016

(86) PCT No.: PCT/US2016/053635
§ 371 (c)(1),
(2) Date: Mar. 20, 2018

(87) PCT Pub. No.: WO2017/053929
PCT Pub. Date: Mar. 30, 2017

(65) Prior Publication Data
US 2019/0060587 A1    Feb. 28, 2019

Related U.S. Application Data

(60) Provisional application No. 62/222,861, filed on Sep. 24, 2015.

(51) Int. Cl.
*A61M 15/00* (2006.01)
*B65D 83/06* (2006.01)
(Continued)

(52) U.S. Cl.
CPC ...... *A61M 15/004* (2014.02); *A61M 15/0005* (2014.02); *A61M 15/009* (2013.01);
(Continued)

(58) Field of Classification Search
CPC .............. A61M 15/00; A61M 15/0001; A61M 15/0003; A61M 15/0005; A61M 15/0008;
(Continued)

(56) References Cited

U.S. PATENT DOCUMENTS

| 5,113,855 A | 5/1992 | Newhouse |
| 5,215,221 A * | 6/1993 | Dirksing ................. A61J 1/067 |
| | | 169/30 |

(Continued)

FOREIGN PATENT DOCUMENTS

| EP | 2013/071309 A1 | 4/2014 |
| GB | 2014/053565 A1 | 6/2015 |
| GB | 2520962 A | 6/2015 |

OTHER PUBLICATIONS

International Search Report of PCT Application No. PCT/US2016/053635 dated Jan. 26, 2017: pp. 1-3.
(Continued)

*Primary Examiner* — Joseph D. Boecker

(57) ABSTRACT

The multi-chambered well dosage form and device disclosed herein can be single or multi dose capable for administration of pharmaceuticals of a range of particle sizes. The present dosage devices and systems provide for improved efficiency and patient ease of use owing to its compact size and simple design, low cost, and consistent, contamination free dosing of dry powder medicaments or other agents. The present disclosure provides a multi-chambered dosage form containing dry powder medical composition containing chamber well with an internal piercing device and one or more adjacent gas-filled chamber wells to aid the dispense of the
(Continued)

powder contents to the user and in certain embodiments, without the requirement of an external energy sources common with active devices known in the art. Said methods, systems and devices provide increased ejection fraction and hence greater efficiency of drug delivery above that as provided by current devices.

12 Claims, 9 Drawing Sheets

(51) Int. Cl.
  *B65D 75/32*  (2006.01)
  *A61M 16/14*  (2006.01)
  *B65D 75/70*  (2006.01)
  *B65D 75/36*  (2006.01)

(52) U.S. Cl.
  CPC .... *A61M 15/0035* (2014.02); *A61M 15/0061* (2014.02); *A61M 16/14* (2013.01); *B65D 75/328* (2013.01); *B65D 75/368* (2013.01); *B65D 75/70* (2013.01); *B65D 83/06* (2013.01); *A61M 15/0008* (2014.02); *A61M 15/0036* (2014.02); *A61M 2202/0266* (2013.01); *A61M 2202/064* (2013.01); *B65D 2221/00* (2013.01)

(58) Field of Classification Search
  CPC ............ A61M 15/0028; A61M 15/003; A61M 15/0033; A61M 15/0035; A61M 15/0036; A61M 15/004; A61M 15/0045; A61M 15/0051; A61M 15/0056; A61M 15/0061; A61M 15/009; A61M 2202/0266; A61M 2202/064; A61M 16/14; A61M 35/003; B65D 83/06
  See application file for complete search history.

(56) References Cited

U.S. PATENT DOCUMENTS

| | | | |
|---|---|---|---|
| 5,655,523 A | 8/1997 | Hodson | |
| 7,669,597 B2 | 3/2010 | Sullivan | |
| 7,810,494 B2 | 10/2010 | Harmer | |
| 8,377,009 B2 | 2/2013 | Sullivan | |
| 8,579,856 B2 | 11/2013 | Sullivan | |
| 2005/0263151 A1 | 12/2005 | Hochrainer | |
| 2006/0169278 A1* | 8/2006 | Djupesland | A61M 15/0028 128/200.14 |
| 2007/0051362 A1* | 3/2007 | Sullivan | A61M 15/08 128/200.23 |
| 2008/0275404 A1 | 11/2008 | Hansen | |
| 2010/0331765 A1* | 12/2010 | Sullivan | A61M 11/06 604/24 |
| 2012/0074176 A1* | 3/2012 | Sullivan | A61M 15/0028 222/541.2 |
| 2012/0138148 A1 | 6/2012 | Harutyunyan | |
| 2012/0259277 A1* | 10/2012 | Shay | A61M 15/0028 604/58 |

OTHER PUBLICATIONS

Written Opinion of PCT Application No. PCT/US2016/053635 dated Jan. 26, 2017: pp. 4-14.
Supplementary Partial European Search Report in counterpart related European Application No. EP16849836.8 dated Apr. 12, 2019. (References included in the report but not cited herein were previously made of record.)

* cited by examiner

DEVICES AND SYSTEMS FOR AIR ASSISTED DRY POWDER ADMINISTRATION

CROSS-REFERENCE TO RELATED APPLICATIONS

The present application claims benefit of priority under 35 U.S.C. § 119(e) to U.S. Provisional Application 62/222,861 filed Sep. 24, 2015, the entire content of which is incorporated herein by reference for all purposes.

REFERENCE TO SEQUENCE LISTING, A TABLE, OR A COMPUTER PROGRAM LISTING COMPACT DISK APPENDIX

Not Applicable

FIELD OF THE INVENTION

The present invention is in the technical field of medical devices. More particularly, the present invention is in the technical field of medical devices for the administration to humans and non-human animals of drugs, biologics, botanicals, probiotics, medical compounds, and pharmaceuticals as powders to the eye, ear, topically to the skin, orally, intra-nasally, lungs, or to sublingual or buccal areas in the oral cavity of humans or other mammals.

BACKGROUND OF THE INVENTION

Certain diseases and medical conditions that are systemic, intra-cranial or local are treatable via the administration of drugs and therapeutic agents taken topically or systemically through the eye, ear, mouth, nose, lungs or dermal skin layer. There are a growing number of medicaments that are most effectively manufactured, stored, delivered, and administered as a dry powder formulation. A number of pharmaceutical agents are deliverable as powders or particles orally to the lungs, sublingual, buccal or intra-nasally (including nose to brain), and may be administered for topical, systemic or intracranial deposition, including but not limited to antibiotics, antipyretics, anti-inflammatories, biologics, biosimilars, vitamins, botanicals, co-factors, enzymes, inhibitors, activators, nutrients, vaccines including DNA based killed or live virus or microorganisms, nucleic acids, proteins, peptides, antibodies, peptide mimetics, prophylactic or therapeutic immune-modulators, anti-viral and anti-bacterial compounds, biologics, diagnostic agents and other agents, pharmaceutical compositions or medicaments.

Solid formulated medicaments have a number of recognized advantages. Compound stability for certain agents is greater in solid form especially polypeptide and protein based biologics whose conformational and higher structure may tend to degrade or denature when in solution thus affecting their biological activity. Similarly, certain drug chemical compounds may tend to dissociate and degrade due to incremental pH shifts, Van der Waals and other forces resulting in diminished shelf life and drug efficacy. Consequently, unstable medicaments formulated as liquids must be refrigerated or even frozen to preserve their potency or effectiveness which adds cost and complicates deployment. This is especially troublesome in such cases whereby vaccines and other unstable medicaments must be distributed to remote areas and underdeveloped regions or very rapidly to large populations during a public health crisis under austere field conditions. Often unstable drugs must then be shipped in solid form and reconstituted back to liquid form at the time of administration thus delaying deployment and adding expense and the need for skilled personnel for proper utilization.

In certain other cases medicaments are designed in solid form to facilitate controlled release to result in sustained pharmacological concentrations of active ingredients over an extended period of time. For systemic treatments, powder based drugs delivered to mucosal surfaces via the nose, lungs or oral cavity offer a number of advantages including rapid drug uptake due to large mucosal surface area capable of systemic uptake, the avoidance of the harsh environment of the stomach and intestinal tract as in the case of pills, tablets, and capsules, and the avoidance of broad systemic and side effects often associated with parenterally administered drugs. Other advantages include enhanced bioavailability, reduced dose volume, and improved patient compliance and ease of self-administration. Powders can be formulated and dispensed to deliver medications topically to wounds, into the ear or nose to reach the upper respiratory tract for the treatment of a localized condition or as a prophylactic.

Typically these agents and medicaments are formulated and prepared from solution by recrystallization followed by milling, but for improved control over particle crystallinity, shape, mean size, and size distribution; lyophilization or various spray drying techniques known in the art are relied upon to produce a bulk powder with precise characteristics to aid in administration. Key characteristics include primarily the mean particle size as well as the distribution of sizes within the bulk powder. For a given inspiratory velocity initiated either nasally or orally, a certain mean particle size and mass is required to result in deposition to the targeted tissue location within the targeted area within the respiratory tract. Generally, smaller particles will tend to deposit deeper in the respiratory tract, more particularly; particles of 3 or fewer microns in diameter have a greater probability to reach the tissues of the lower lungs, with even smaller aerodynamic diameters preferred for enhanced systemic uptake. Conversely, larger particles of greater than 5 microns to the tens of microns or larger, owing to their larger mass are more likely to deposit proximally to the point of administration; most typically within the nasal cavity and passages when administered intranasally, or in the oral cavity or pharynx, larynx, or trachea if orally administered. The dispersity or polydispersity index describes the range and proportion of sizes within the bulk powder. Depending upon the targeted application location, a less disperse or monodisperse powder may be desired to assure a specific deposition location or a more disperse powder may be necessary in order to impact a larger range of tissues such as the case with certain anti-viral therapies and vaccines where the intent is to contact the virus residing in several tissue areas and locations with the respiratory tract.

Other aspects of powder engineering are intended to impact the flowability, absorption efficiency and reduce the aggregation of the powders in order to aid in the friability of the material to increase the delivery efficiency, efficacy and rate of uptake. For that reason, certain excipients, carriers, or other matrix components may be added in defined quantity to the active dry pharmaceutical agent to impact particle shape, texture and surface properties for reduced adhesive and electrostatic forces in order to facilitate the breaking apart of settled or aggregated particles prior to and during dispense. Other excipients, carriers, or other matrix components may be added in defined quantity to the active dry pharmaceutical agent to impact mucosal absorption or dwell time on the targeted deposition site. Further, micro and nano particle formulations of drugs are often employed using biocompatible and degradable polymers as carriers.

All of these and other powder engineering principles play an important role in conjunction with the design of packaging and dispensing systems and devices to achieve precise delivery and dispense characteristics of powdered drugs. A variety of packaging and devices are known for delivering a controlled quantity of a dry pharmaceutical preparation to the ear, dermis, nose, nasal mucosa, sublingual, buccal, oral mucosa, pharyngeal, tracheal, and lower respiratory tissues.

Unlike liquid drug formulations, whereby a simple pump can deliver a precisely controlled quantity of drug as droplets with the required spray characteristics; drugs formulated as dry materials present additional challenges owing to the propensity of powders to settle and physically and chemically agglomerate. Thus it is necessary that the device must not only contain a single dose of material or be capable of metering it from a bulk source, but must also impart sufficient energy to agitate the material to break up the particles and propel them to the deposition site in the correct quantity and mean particle size in order to provide optimum deposition characteristics, and consequently the most advantageous therapeutic effect.

There exists numerous systems and devices to dispense powders to a human or other type of mammal; the basic designs of which vary depending upon the site of administration, target deposition zone and intended topical, systemic or intracranial application. For example, Dry Powder Inhalers (DPIs) is the class of devices that is a common type of device for delivering dry pharmaceutical preparations to a user most typically for pulmonary deposition via oral administration. Typically such devices require an external propellant, pressurizer or other external energy source which classified those devices generally as Active Dry Powder Inhalers (ADPIs). Alternatively, other devices rely solely on the inspiratory airflow of the user and hence are breath actuated and referred to as Passive Dry Powder Inhalers (PDPIs). Both approaches suffer from significant drawbacks. In the case of ADP's, owing to the need for a propellant or electromechanical componentry and often bulk storage of drug; the device itself can be complex, large, expensive, cumbersome, and inconvenient to handle and use. Passive devices while often smaller, less expensive and containing one or more individualized unit doses; often deliver inconsistent quantity of drug to the user with the variability of delivered dose a function of user inspiratory flowrate. Further, the passive devices often operate at a reduced efficiency as given by the fraction of the dose quantity actually delivered to the user. The reduced efficiency diminishes the cost effectiveness of the passive devices due to wasted drug material. The undispensed portion of the drug that remains is also left behind to contaminate the device, and in the case of multi-dose devices, possibly contaminate subsequent doses of drug.

In the case of pulmonary deposition, very small particles (1-5 microns) are preferred but smaller particles typically suffer from an increased tendency to form clumps due to hygroscopicity, adhesion and electrostatic forces. Prior art devices commonly rely on high velocity propellants or electromechanical agitation to de-aggregate the powder particles and deliver the material to the target deposition zone of the user. The means of providing the external energy source are widely varied and include pressurized canisters, propeller type agitators, mechanical, solenoid or piezoelectric based vibration to aid in particle deaggregation and delivery. For example, Gumaste in U.S. Pat. No. 7,950,390 discloses a microelectronic piezo vibrator to aid breaking apart the agglomerated particles and suspending them into the flow field. Such microelectronic systems offer improvements in the bulk size of the device as compared to Wilke et. al., who in U.S. Pat. No. 3,948,264 discloses a battery driven electro-mechanical vibrator to facilitate dispersion and release of the particles. These schemes, while incrementally different, consistently suffer from the disadvantage of system complexity due to the need for circuitry, motors, and electrical power sourcing. Additionally, these prior art devices often entail capsule based dosage forms externally pierced by various means often including retractable mechanical or motor driven pins, often arranged in multiple pin arrays and channels to facilitate increasing the fraction ejected from the dosage form.

Alternatively, passive devices rely upon the forceful inhalation of the user to disperse the particles and deliver them to the airway and the targeted tissues. In most prior art active and passive devices, the operation often entails a series of steps to facilitate administration of drug. Additionally, the dosage forms are often singularized into the form of capsules containing the prescribed dose quantity that must first be externally pierced in order to expose the compound to the velocity field. The other dosage form common in such devices are individual blisters either singularized or in strips or cartridges that are loaded into the dispensing device and also first require either piercing of the blister or peeling of the upper lidding layer to expose the contents. For example, Davies et al in U.S. Pat. Nos. 5,590,645; 5,860,419; 5,873,360; 6,032,666 discloses an inhalation device with a multi-dosage configuration in the form of a strip of individual blisters containing the medicament. The base and lid materials are peeled apart as the strip is rotated into an opening station position and the two ends taken up on separate spools. Once in position and the contents exposed, the user then inhales the drug compound. This prior art device has the advantage of simplicity owing to the reliance upon the users inhalation as the primary means of particle dispersion and delivery. However, that approach may result in poor dose consistency; as measured by patient to patient variability or dose to dose variability of an individual patient. This variability is a consequence of the natural range of possible patient inspiratory rates and velocities. Further, the passive scheme as disclosed whereby no means are provided to augment the ejection of the blisters, may result in incomplete dosing and low efficiency of delivery whereby medication is left in the blister. Further, the undelivered quantity continues to reside within the opened blister and once indexed may fall out into the device interior, contaminating both the device and possibly subsequent doses.

Various devices within the prior art include measured quantities of dry powdered formulations and pharmaceutical compositions contained in a crushable ampoule, blister or other dosage form that entail forcing the form against an external piercing device during use, in order to pierce the dosage form and release the contents. The inherent disadvantages involve the reliance on external energy sources and/or solely upon the inhalation force of the user to adequately break apart the settled and aggregated dose material into individual particles. Often such prior art devices incorporate various aspects on the exterior of the dosage form or in the device itself such as channels, variously configured inlets, outlets, and orifices or other turbulence promoting means for improving the dispersion of the particles.

However, such schemes typically result in modest improvement in dose efficiency. The present invention addresses these disadvantages in the prior art devices by providing for an internally pierced dosage form that also includes one or more adjacent gas filled blister chamber(s) expressed in a manner to provide improved powder dosage delivery efficiency. Device technology has lagged current powder formulation and powder engineering capabilities such that the enhanced precision and effectiveness of new and existing powdered drugs can be fully harnessed. The present disclosure provides dosage forms with integrated dispense energetics for delivery of predetermined quantities of dry powder or granular pharmaceutical or medical compositions for local, intracranial and/or systemic action. Integrating the device energetics into the dosage form reduces overall device cost, complexity, and bulk to improve patient compliance and ease of use.

SUMMARY OF THE INVENTION

Various embodiments of the present invention provide for a dry powder unit dose device for the storage and administration of dry powder formulated pharmaceuticals. The device comprises a dosage form with more than one blister well. Blister wells of the device contain the powder medicament, an internal piercing device, and a gas propellant. The gas propellant is in fluid communication with a dispensing well which, upon rupture of a frangible sealed interface between the propellant containing and dispensing wells, provides for de-agglomeration, entrainment and propulsion of the powder.

According to additional embodiments of the present invention, a delivery system for administering a dry powder substance to a subject is provided. The system comprises a dispensing device, at least one dry powder unit dosage form with multiple blister wells containing the powder to be delivered, an internal piercing device, and gas propellant. The gas propellant is in fluid communication with a dispensing well which, upon rupture of a frangible sealed interface between the propellant containing and dispensing wells, provides for de-agglomeration, entrainment and propulsion of the powder to a subject.

BRIEF DESCRIPTION OF DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
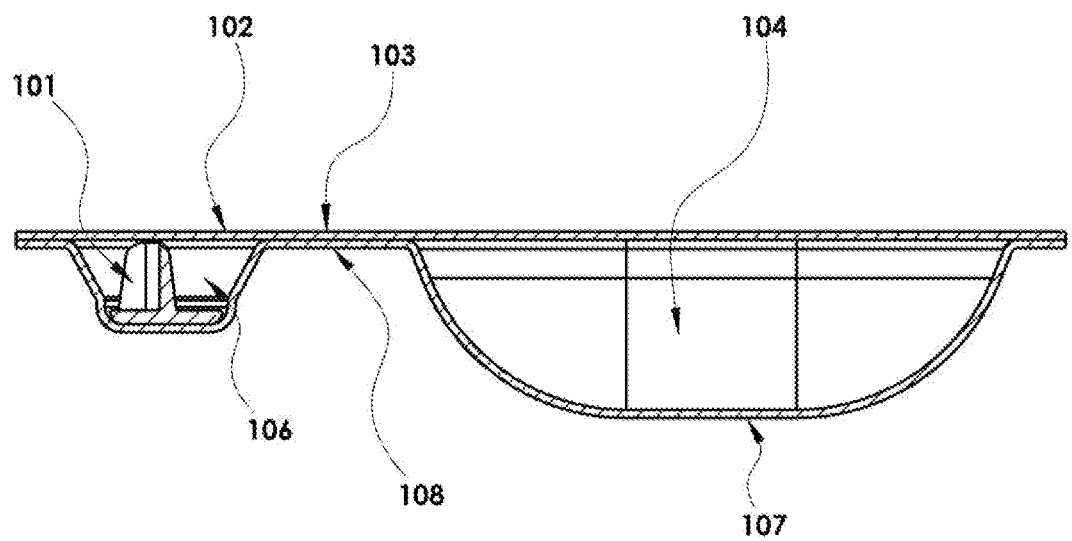
FIG. 1 is a side view in longitudinal section of a two-chamber dosage form showing piercing device, powder, and temporary inter-chamber seal.

The following description of the embodiments refers to the accompanying drawings. The same reference numbers in different drawings identify the same or similar elements unless indicated otherwise. The following detailed description does not limit the invention. Instead, the scope of the invention is defined by the appended claims.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Throughout this disclosure, unless the context dictates otherwise, the word "comprise" or variations such as "comprises" or "comprising," is understood to mean "includes, but is not limited to" such that other elements that are not explicitly mentioned may also be included. Further, unless the context dictates otherwise, use of the term "a" or "the" may mean a singular object or element, or it may mean a plurality, or one or more of such objects or elements.

The present invention provides dosage forms of multi-chambered wells with at least one chambered well containing internal componentry which provides for piercing or opening of the form from the inside, and pressure assisted agitation and expression of the drug contents to aid in dispersion and dispensing of the drug to a user. Note herein that said dosage forms are commonly referred to in the art using alternative terms as forms, units, unit dose or dosage forms, blisters, blister packs, blister wells, wells, chambered wells, ampoules, or similar terminology. The dosage forms described herein generally as "forms", "unit dosage forms", "wells", "blisters" or "chambered wells" etc. are used interchangeably and are intended to encompass the full scope of known formed receptacles commonly in use for pharmaceutical substance storage and delivery.

The dosage forms may contain in certain embodiments a biologic, a biological agent, diagnostic agent, or a small or large molecule pharmaceutical drug compound. The drug dosage forms are for use in delivery devices that deliver the drug compound as a dry powder, particles, granules or other agent or formulation as a dry material to a human or non-human animal. The dosage forms can be used, for example, to deliver one or more measured doses of a dry pharmaceutical, biologic or medical composition to the ear, nose, brain, nasal passages, mouth, throat, trachea, pharynx, upper or lower airways to include into the lungs, or to a topical location of a user for the therapeutic or prophylactic treatment of local or systemic conditions.

Any powder or dry form pharmaceutical is contemplated in the present disclosure, including but not limited to antibiotics, antipyretics, anti-inflammatories, biologics, botanicals, probiotics, vitamins, co-factors, enzymes, inhibitors, activators, nutrients, aptamers, thioaptamers, anti-virals, immuno-modulators, diagnostic agents, vaccines including killed or live virus or microorganisms, nucleic acids, proteins, peptides, antibodies, peptide mimetics, micro or nanoparticles, or other agents known in the art. The following is a limited list of examples of general classes of medicaments administered through the nasal or oral cavity or topically to the eye, ear or skin as dry powders for a host of indications which can include but not limited to anemia, asthma, bronchitis, rhinitis, flu, cancer, cystic fibrosis, diabetes, osteoporosis, hepatitis, arthritis, chronic or acute pain, immunodeficiency disorders, multiple sclerosis, endocrinological disorders, neurodegenerative disorders, ocular disorders, metabolic disorders, dermal disorders and wounds, etc. Drug compounds for treating those indications include various adjuvants, calcitonin, erythropoietin, heparin, inhibitors, insulin, interferons, interleukins, hormones, neurotropic agents, growth factors, stimulating factors, vasodilators and constrictors, etc. This list is not intended to be exhaustive and in no way is inclusive of all possible conditions and diseases, drugs and compounds, or routes or targets of administration, but rather is to illustrate the breadth of dry powder drugs and indications employable in the present invention and contemplated by the present disclosure.

In certain embodiments, the medical compositions are in the form of a powder, or a dry pharmaceutical combined with one or more active agents and combinations of pharmaceutically acceptable carriers or materials to include matrix agents, diluents, preservatives, coatings, adsorption or absorption enhancing or delaying agents, excipients, salts, bulking or filling agents, anti-clumping agents, adjuvants, buffers, chelators, or other ingredients known to those in the art as needed to affect the drug's stability, flowability, adhesion, dispersion and deaggregation characteristics, or pharmacological uptake, efficacy, activity and rate of release. For example, in certain embodiments a predetermined quantity of biological or pharmaceutical material may be combined with mannose, lactose or other carrier or bulking agents known in the art. The drug may also be bound to or encapsulated within nanoparticles or other macromolecules to aid in stabilizing the drug and/or affecting the drug compound's rate of release over time. Any conventional media or agent compatible with the active agent is contemplated. More than one active agent may also be incorporated into the compositions, for the same or separate purposes. The phrase "pharmaceutically acceptable" refers to compounds and compositions that are appropriate for administration to humans or non-human animal.

The present disclosure provides crushable dosage forms that contain the dry powder as well as an internal piercing device that opens the dosage form and provides a communication channel for delivery of the powder from the blister to the user and includes one or more additional formed chamber wells pressurized to aid in the expression of the powder.

In preferred embodiments, the energy source for particle break up, dispersion, and delivery is provided by the user's hand force during the mechanical actuation of the multiple-chambered blister form. In certain embodiments the user driven device actuation force may be combined with or augmented by additional external energy supplying devices and such embodiments are fully contemplated herein.

In certain embodiments the crushable unit dosage forms of the present disclosure are blisters that can be manufactured as described by Nelson in U.S. Pat. No. 7,963,089 and incorporated by reference in its entirety herein. The manufacturing processes for forming blister wells for unit-dose packaging in a continuous web can include a step of drawing a metal, polymer, or laminated metal-polymer foil or other suitable sheet of material with the appropriate mechanical characteristics to allow hot, warm or cold forming and drawing are known in the art and contemplated herein. In certain embodiments, one or more plungers can be used to form a primary contour, the contour having a depth of at least 100% and up to 150% of the depth of the final formed recess or well. A second stage involves shaping the primary contour with one or more of the same or additional plunger(s) to the desired formed recess depth and shape, with a depth that is less than the depth of the primary contour, while substantially maintaining the surface area of the primary contour formed in the first stage. The contour or shape of the blister well can be formed to contain certain shape features, indentations, or be imparted with texture by the forming pins to provide for a means of securing the internal piercing device within the blister well or recess. The formed well or recess is then loaded aseptically with the predetermined quantity of sterile or non-sterile dry powder and the internal piercing device and a lidding material of the same or similar laminated material as the blister well or other sheeting material can be rolled atop the recesses and bonded to the well sheeting with adhesives, or by thermal or ultrasonic or other welding means.

The mass and volume of particles dispensed from an individual blister are various depending upon the blister shape and volume, the required volume of headspace gas, and the powder characteristics, which are primarily the bulk density which is affected by the particle shape, size, and adhesion and aggregation properties, among others. For example, the dosage mass and volume for intranasal or orally administered pulmonary treatments can range from 1 to 50 milligrams and 10 to 100 microliters, respectively. This is but a single typical range for one application; ranges for other indications and routes of administration and needed therapeutic quantities can vary substantially and are contemplated herein to include ranges to gram level masses and 1000 microliters dose volume or more for certain topical administered compounds.

In certain embodiments, the individual dosage forms or blisters that can be formed in sheets which are in later manufacturing steps, singulated into individual doses for use in single-use, disposable, non-reloadable devices, or for use in devices which are reloadable with additional unit doses for subsequent dosing of the same or different patient(s). Alternatively, and depending upon the application and indication, the sheets may be formed and cut into rows, arrays, grids, disks, or other configurations of blisters suitable for use in multi-dose devices. Regardless of the shape, size, or geometric configuration of blisters, ampoules, or wells; each unit contains an internal piercing element.

Certain preferred embodiments of the present disclosure can include a dosage form comprising two or more adjacent wells formed as described earlier, and sealed with a single contiguous lidding. In the case of two or more adjacent wells, the perimeter surrounding the plurality of adjacent blisters is sealed permanently, using in various embodiments including adhesive coated surfaces, heat and/or pressure application, ultrasonic vibration welding or other suitable methods known in the art to attach opposing seal faces of coated metal or metal polymer laminates commonly used in the manufacture of dosage forms. The space between adjacent dosage and gas filled blister wells can be left unsealed, or perimeter sealed, or other configuration resulting in a partial or full seal that provides a frangible sealing method to maintain separation of the contents of the adjacent blister wells until such time as it is desirable to provide communication between adjacent blister wells.

There are several methods of manufacturing the temporary frangible seal; including the creation of a tortuous or elongated path by crimping together the layers of foil or film, or, preferably to attach the layers using a weak adhesive, heat, or ultrasonically generated bond. Numerous commercially available laminated structures, manufactured using known materials and methods which facilitate the production of variable strength of seal between opposing faces are known in the art and are readily contemplated by the present disclosure. For example, co-assigned U.S. Pat. No. 8,683,995 for production of multi-chamber dosage forms is hereby incorporated by reference herein in its entirety for all purposes.

Multi-chambered dosage forms comprising at least one blister well adjacent to the powder containing dosage form have the advantage of ease of customization of blister size, shape, and orientation of the individual forms. Certain preferred embodiments include two adjacent wells, one well containing a piercing device and the dry pharmaceutical powder and an adjacent well of similar or different geometry containing the gas that acts as a propellant and dispersant. In such an embodiment the two wells are maintained separate via one of the aforementioned sealing techniques until the user acts on the dispensing device, compressing the gas-filled chamber well, which ruptures the seal and opens a pathway between the blister wells. Sequentially timed or substantially contemporaneous compression of the dosage blister well results in the piercing the powder-containing blister well and expressing the powder aided by the gas flowing from the gas filled blister well.

In another exemplary embodiment, the plurality of wells comprises three adjacent wells, the gas-filled, pharmaceutical powder, and piercing device are held in separate wells together which are permanently sealed with a single lidding layer and each is temporarily separated from adjacent wells until the dispensation action is initiated. In the case of three wells, the sequence of events that comprise the dispense includes compression of the gas-filled blister well, rupture of the temporary seal between gas-filled blister well and powder blister well, rupture of the temporary seal between powder blister well and piercing device blister well, and crushing of the piercing device blister well, causing the piercing device to pierce the lidding allowing powder to escape through the pierced lid, entrained in the pressurized gas propellant.

The dosage form can be a crushable blister containing a powder medical composition. The blister well can be sized to permit sufficient volume to contain both the prescribed dose quantity of dry powder material loaded into the blister as well as a headspace of free gas volume that remains to permit pressurization and agitation of the contents. Such dosage forms are for use in delivery devices and systems in which a handheld device that includes an actuation mechanism that can include a ram, piston or plunger which when forced against the dosage form pressurizes the blister contents during the compression phase of the dispense that occurs prior to and during initial breaching or piercing of the lidstock by the internal piercing device. Once pierced, the pressurized and agitated contents are forced out through piercing device's elongated hollow tip internal channel aided by the additional pressure and air flow from the gas-filled chamber.

Dosage Form

Figure 2:
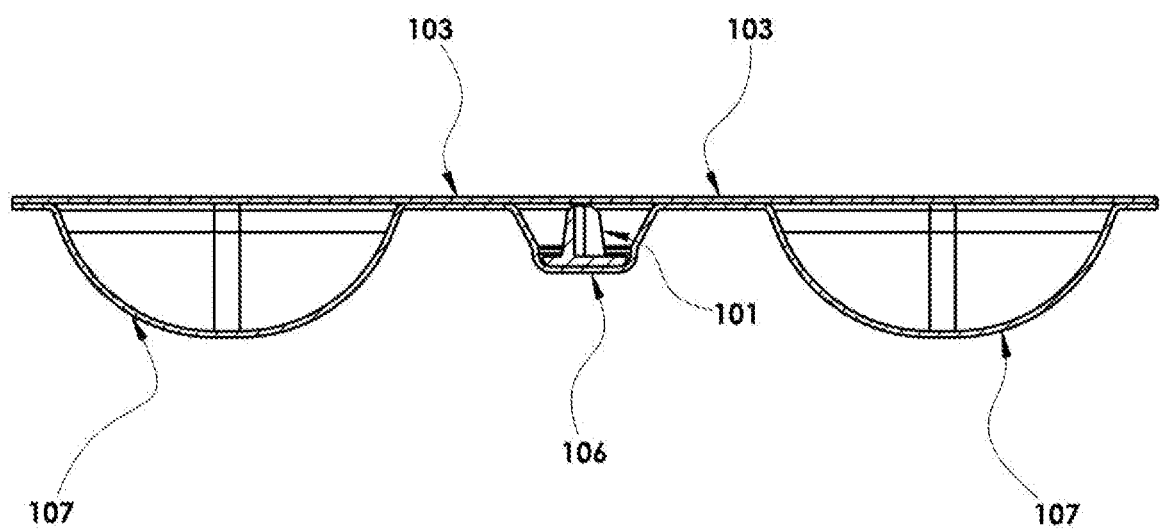
FIG. 2 is an alternative multiple-chamber blister-based dosage form having two propellant chambers, each entering a powder containing chamber through a separate inlet.

The dosage form described herein is in preferred embodiments a sealed multi-chambered (multiple blister wells) container as shown in FIGS. 1-17. FIG. 1 shows for example a two-well dosage form formed from a base material 108 as described above sealed to a lidding material 102 wherein a premeasured quantity of pharmaceutical powder is contained in a powder-containing blister well 106, an internal piercing device 101 inside a dispensing (in preferred embodiments, the same as the powder containing) blister well 106 for opening the package from within, and a premeasured quantity of gas propellant 104 in the propellant or gas containing blister well 107 which upon expression acts to agitate and entrain the dry powder in a velocity stream via a communication path 103 when the user actuates a dose. FIG. 2 shows another exemplary embodiment with two propellant containing wells 107 adjacent to a single powder containing/dispensing well 106 with internal piercer 101. Note that this configuration has two communication paths 103; one between each propellant and the dispensing well. Alternate embodiments include a three-chamber dosage form as given FIG. 3 wherein the propellant chamber 107 exists adjacent to a powder only containing well 134. Adjacent to or in proximity of the powder-containing well is a piercing device only containing dispensing well 106.

A dosage form is a blister well fabricated using one of numerous methods known in the art to manufacturers of blister packaging; including methods described in Nelson U.S. Pat. No. 7,963,089 and incorporated herein for all purposes. In an example, the final dosage form includes a series of adjacent formed wells as shown in cut-away view in FIG. 4 with the contents as previously described sealed within the powder and propellant containing wells (106, 107) using a lidding film attached to the blister forms with a common perimeter seal 171.

A communication path 103 between the gas propellant filled well and the adjacent well or wells (e.g. powder-containing well, dispensing well, or combination powder-containing and dispensing well) are provided such that, during manufacture and storage prior to use, the contents of the wells adjacent to the propellant well are maintained separate from the gas propellant filled well(s). At the time of use [see, for example, sequence in FIGS. 11-13], the propellant is transferred from the propellant-containing well 107, via a communication channel 103 and through the powder-containing blister well 106, agitating and suspending the powder in the propellant and out of the dosage form through the opening in one part of the sealed form (see, for example FIG. 12, 201) by the piercing device 101, preferably in the lidding part 102 of the dispensing blister well 106.

Figure 3:
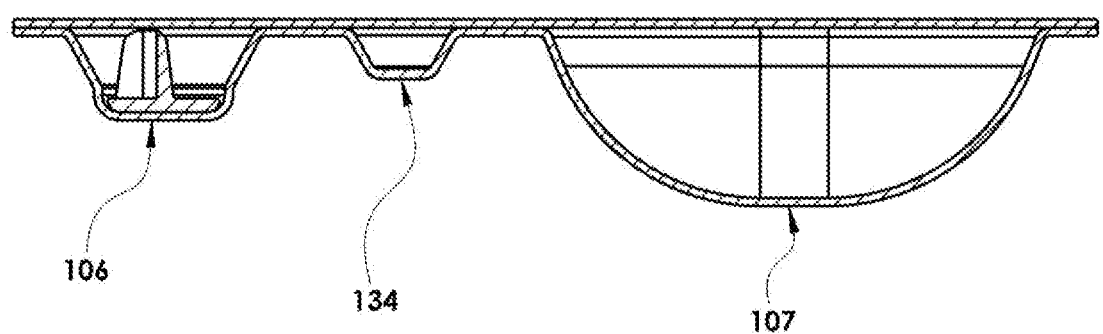
FIG. 3 is alternative multi-chamber dosage form wherein propellant, powder and piercing device are contained in separate adjacent chambers.

An additional embodiment as shown in FIG. 3 contains powder and internal piercing device in the dispensing well 101, 106 adjacent to an intermediate pressure-accumulating well 134, which is adjacent to a compressible propellant well 107. Such an intermediate well may in certain embodiments (not shown to preserve clarity) contain flow paths or turbulence promoting features such as a screen mesh or other device or obstacle known in the art to modify fluid path and pressure.

Piercing Device

In certain preferred embodiments the present invention discloses a dosage form containing an internal piercing device as described herein. The internal piercing device can be manufactured by techniques known by those skilled in the art, for example injection molding or machining. The piercing device can be constructed of any material with suitable chemical compatibility and mechanical properties to impart the design strength characteristics such as ceramic, glass, metal, composites, polymeric plastics etc. In preferred embodiments the internal piercing device may be constructed from polymeric materials to include but not limited to polyethylene (PET), polypropylene, polystyrene, or poly ether ether ketone (PEEK), self-reinforced polyphenylene (SRP) or other pharmaceutical or medical grade material or materials. In preferred embodiments, the internal piercing devices are typically injection molded as single piece components, however in certain other embodiments where certain structural features are less amenable to one-piece molding; the devices can be assembled from multiple machined and/or molded parts. For example, certain embodiments may entail attaching by snap fit or threading a machined metal elongated tip to a plastic base part. Other combinations of parts, manufacturing methods, materials, and assembly methods are well known in the art and fully contemplated herein.

Through experimentation it was determined that piercing devices having a single flow directing channel had a performance advantage over piercing devices that have multiple channels through which powder can travel. Piercing devices with multiple inlets provide one or more constrictions and locations where powder can be trapped due to blockage while the compressed propellant may continue to flow through the unblocked passage or passages and out of the dosage unit. Such blockages typically result in lower powder dispense efficiency and thus lower or more variable dosing. Therefore in certain preferred piercing devices 101 as shown for example in FIG. 5 have a single flow-directing channel 261 running from the base to the piercing tip of the elongated piercing member 262.

Figure 4:
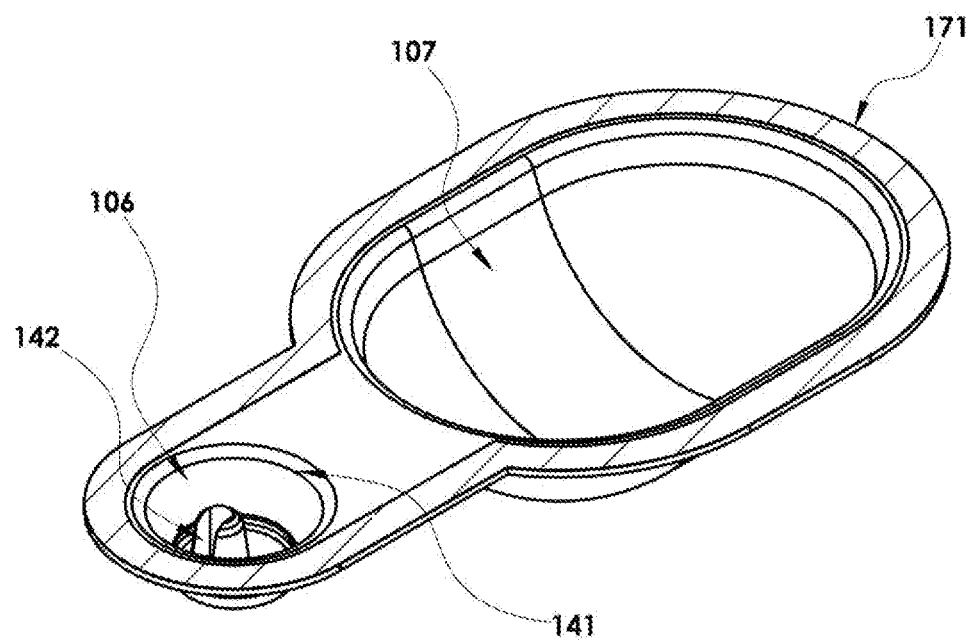
FIG. 4 is an isometric view of a two-chamber dosage form without lidding.
Figure 5:
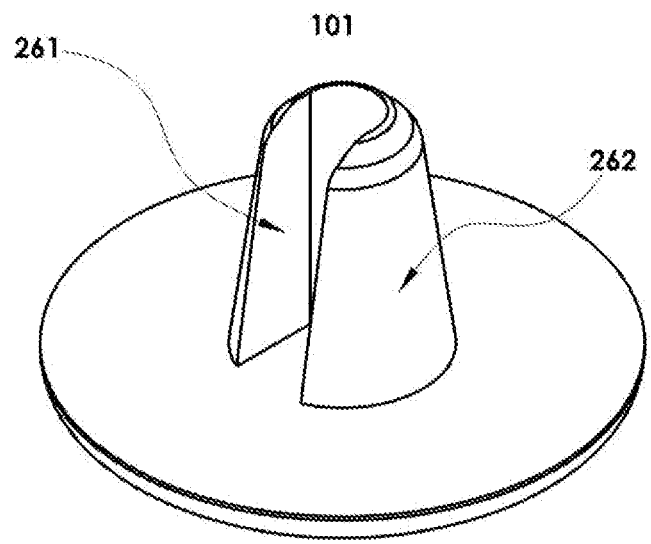
FIG. 5 shows a piercing device with its elongated piercing tip and flow-directing channel centered on the piercer base
Figure 6:
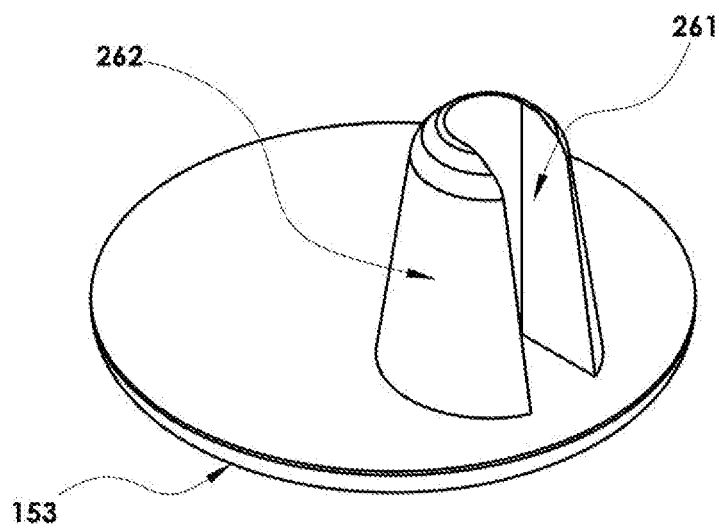
FIG. 6 shows a piercing device with its elongated piercing tip and flow-directing channel positioned off-center on the piercer base.
Figure 7:
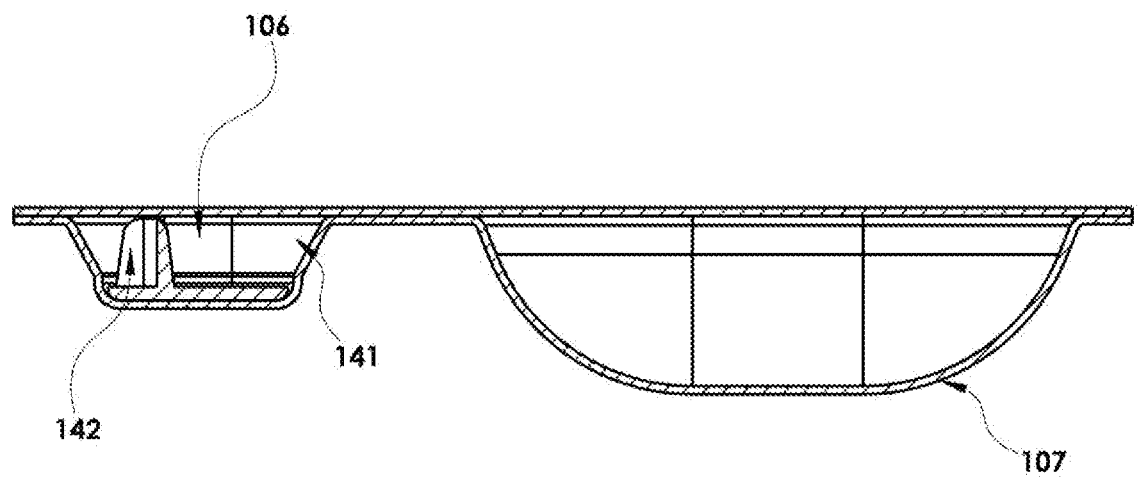
FIG. 7 is a longitudinal section of a preferred two-chamber dosage form, wherein powder and piercing device are contained in a dispensing well, which is elongated to accommodate the quantity of powder required for the product application.
Figure 8:
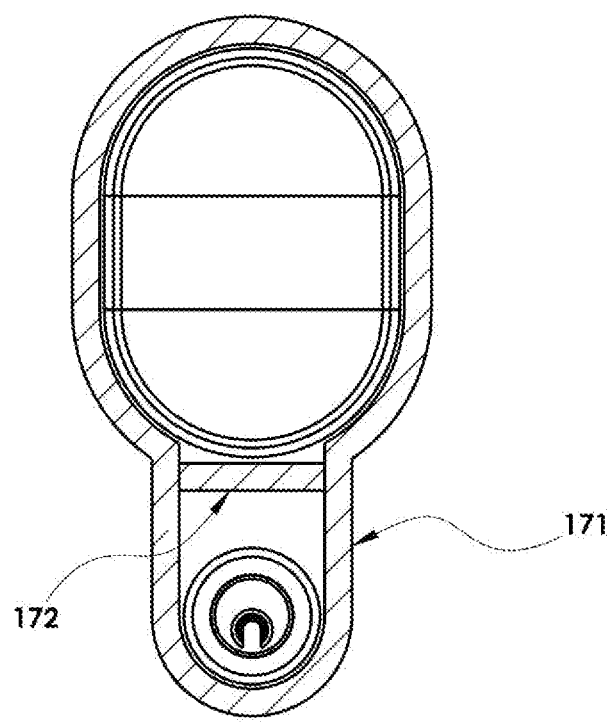
FIG. 8 is a top view of a preferred two-chamber dosage form showing permanent seal and temporary seal regions.
Figure 9:
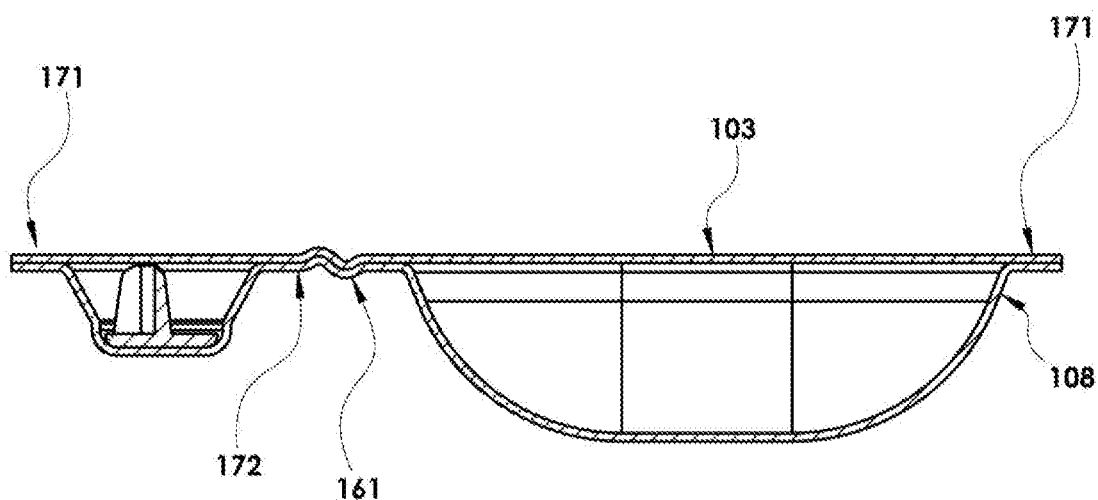
FIG. 9 is a side view in longitudinal section of a preferred two-chamber dosage form showing piercing device, powder, and alternative tortuous path closure.
Figure 10:
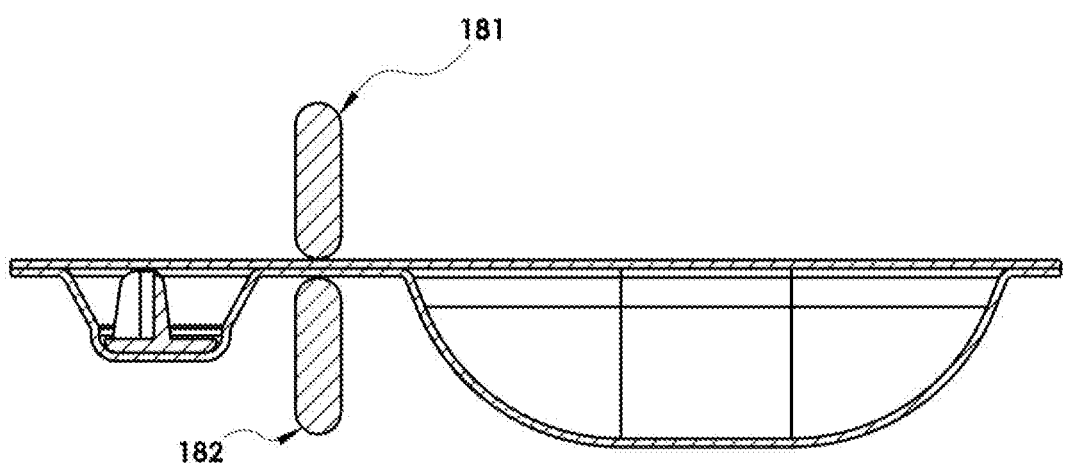
FIG. 10 is a side view in longitudinal section of a preferred two-chamber dosage form showing piercing device, powder, and alternative pinch closure.
Figure 11:
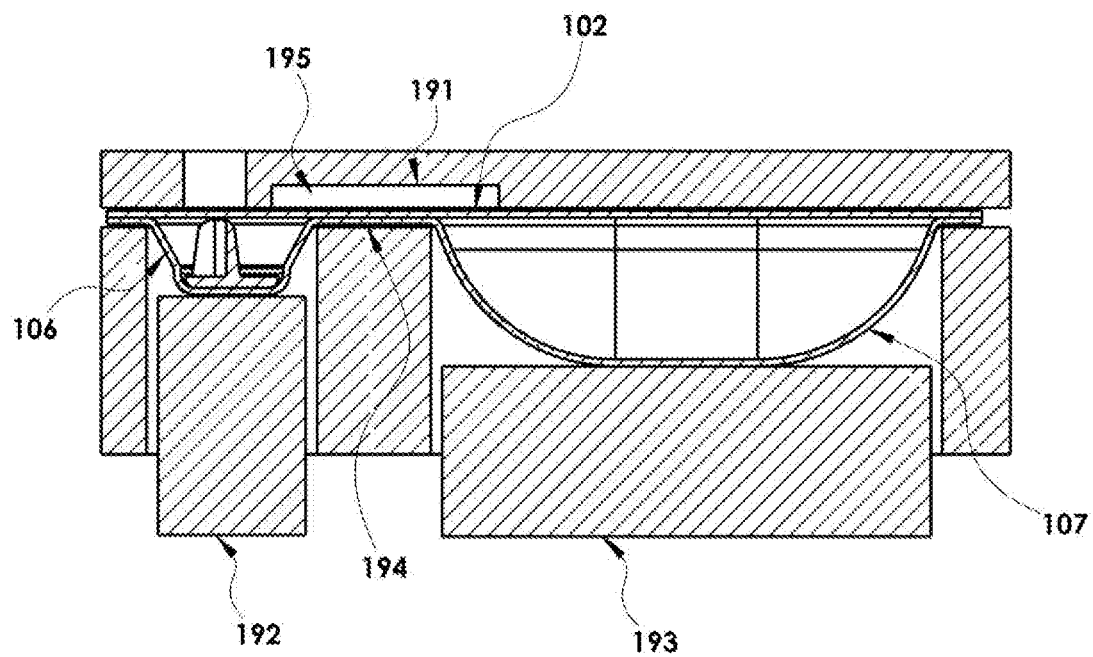
FIG. 11 is a longitudinal section of a dispensing system with two chamber dosage form as in FIG. 1 attached to a dispensing device, showing blister compressing parts of the dispensing device as part of the actuation sequence.
Figure 12:
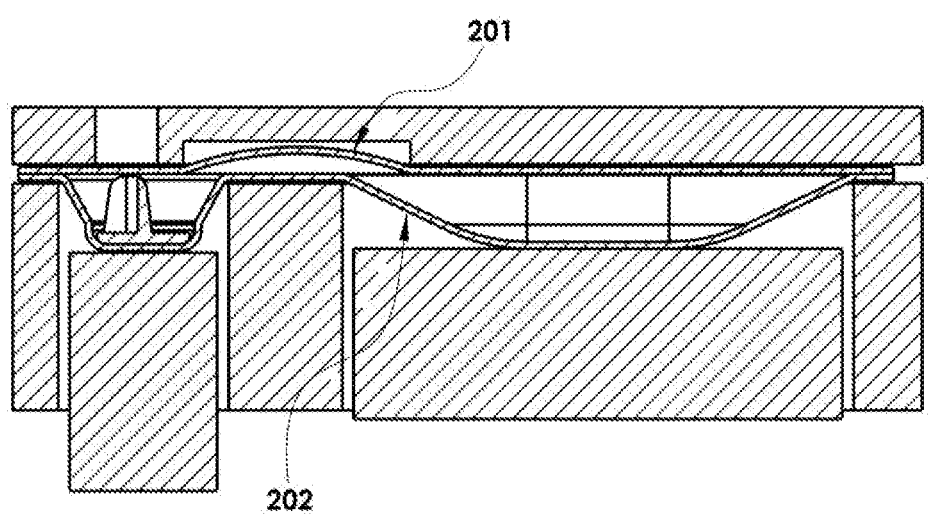
FIG. 12 is a side view in longitudinal section of a two chamber dosage form dispensing system attached to a dispensing device as in FIG. 11 with the propellant chamber compressed.
Figure 13:
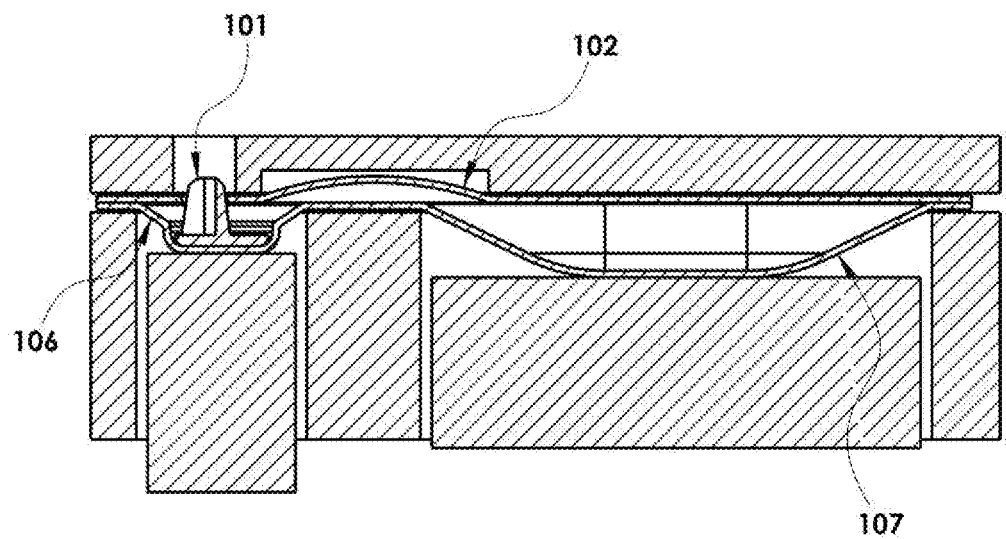
FIG. 13 is a side view in longitudinal section of a two chamber dosage form attached to a dispensing device as in FIG. 11 with the propellant chamber compressed and the powder and piercer chamber compressed with the piercing device puncturing the dispensing blister well lidding.
Figure 14:
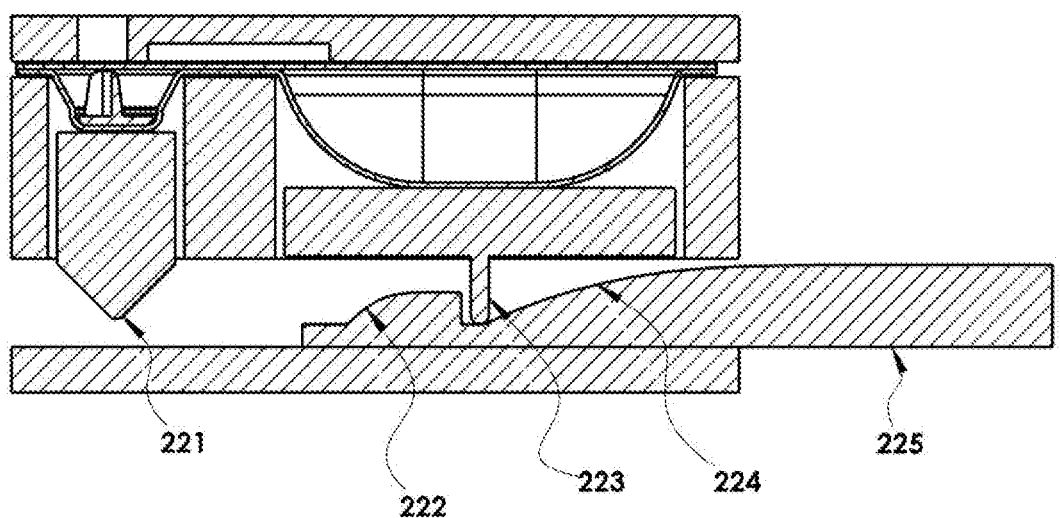
FIGS. 14-16 are side views of a two-cam dispense actuating part used to fix the sequencing and relative timing of compression of the propellant chamber and powder/piercer chamber.
Figure 15:
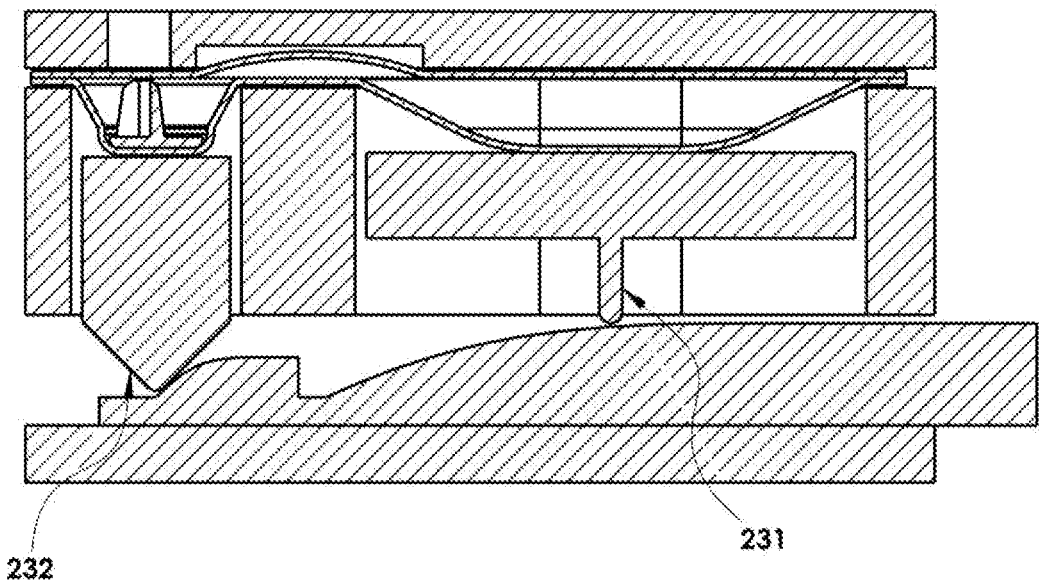
Figure 16:
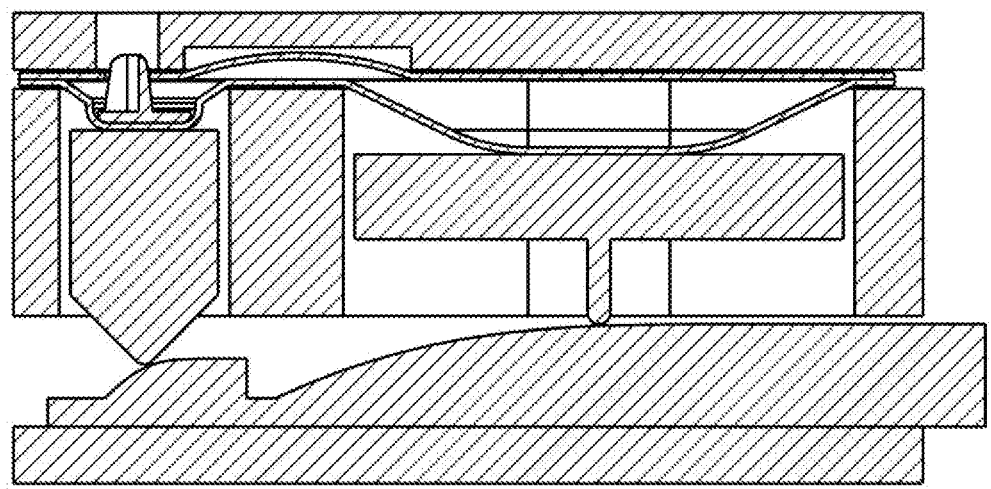
Figure 17:
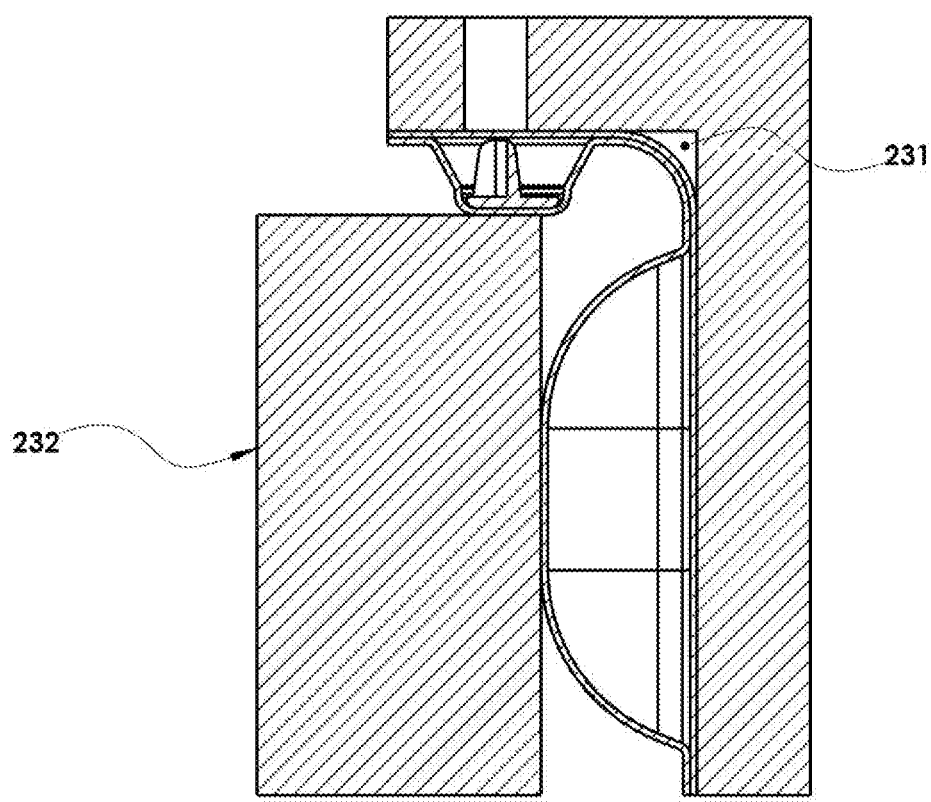
FIG. 17 shows an alternative dosage unit dispensing system with a single mechanical device operating upon orthogonally oriented dispensing and propellant containing wells.

Further, experimentation showed that orienting the flow-directing channel FIG. 5, 261 such that the longitudinal axis of the channel is oriented axially upon the piercer base such that it is substantially opposite the side of the dispensing well where propellant enters is advantageous. See also as shown in top cutaway FIG. 4, 142 and as side view FIG. 7, 142. In addition to the axial orientation of the channel, its later positioning upon the piercer base may offer efficacious advantage. FIG. 6 shows the elongated piercing member 262 located off center on the portion of the elongated piercing member base 153. Inside the dispensing chamber, the offset piercing member would be oriented opposite the end of the dispensing chamber where propellant flows into the chamber as shown in FIG. 4, 141 during dispense thus positioning the disclosed channel as far toward the end of the dispensing chamber opposite the end where propellant flows into the chamber (see also sideview FIG. 7). Such positioning and orientation provides a substantially unidirectional flow of propellant through the powder in the dispensing chamber. This preferred exemplary arrangement generates a higher velocity region of flow very near the flow directing channel. Acceleration of the propellant-powder mixture in the transition from the main region of the dispensing chamber 106 into the flow-directing channel (e.g. FIGS. 4 and 7, 142) of the piercing device provides improved agitation over known methods which more effectively de-agglomerates the powder.

The flow path from propellant blister well into an adjacent blister well during dispense is comprised of a base layer made of forming film (e.g. FIG. 1, 108) opposite a lidding layer of forming film 103. Opposing layers of forming material are sealed together along the periphery of the flow pathway by a common perimeter seal 171. In certain embodiments, this flow pathway provides a temporary seal across the pathway such that upon fabrication and storage, the contents of adjacent wells are maintained as separate until the temporary pathway seal is ruptured or disturbed during the dispense process, or as a preparatory step immediately prior to dispensing from the dosage unit.

An exemplary embodiment of a temporary seal across the inter-blister flow path is shown in FIG. 8. The adhering of the two opposing film layers comprising the walls (FIG. 1, 108, 103 discussed above) of the flow path 172 using sealing methods known to manufacturers of blister packaging, including those described in Sullivan U.S. Pat. No. 7,669,597 incorporated herein in its entirety for all purposes. This temporary seal holds the two opposing layers together in a weldment of a bond strength which is weaker than the strength of the permanent perimeter seal 171 until internal pressure caused by compression of the propellant e.g. FIG. 12, 202 during dispense is sufficient to separate the opposing layers of the temporary seal FIG. 12, 201.

An alternative embodiment of the temporary seal is shown in FIG. 9 with the creation of a tortuous elongated path by crimping the opposing layers together as 161 to provide a lengthened pathway for the gas propellant to upon compression of the propellant chamber separates the opposing layers due to the rise in internal pressure.

In yet another embodiment shown in FIG. 10 uses a pinching mechanism 181, 182 mounted to the outside of the dosage unit within the dispensing device described in greater detail below. The pinching mechanism when attached to the dosage unit holds opposing film layers together. Parting of the mechanical components occurs when the user actuates the dispensing device. In one exemplary embodiment, the pinching mechanism is fabricated exists in the pinched state and is forced open using a mechanical leverage arm during the dispense actuation.

Certain exemplary embodiments of the dosage unit may be fabricated is such a way that one or more dosage units can be installed into a separately manufactured dispensing device by the user prior to use, and then replaced with one or more additional dosage units by the user, minimizing the portion of the system that becomes disposable waste after use. Other embodiments are fabricated such that one or more dosage units are installed into a dispensing device during manufacture and the user disposes of the entire assembly after using all dosage units.

Dispensing Device To dispense doses of product from the dosage unit to the desired location by the user, a system to provide the dispensing sequence is needed. The present disclosure contemplates a dispensing device that acts on the dosage form, causing the pharmaceutical powder to be ejected from the dosage unit with the desired efficiency and plume pattern and as well as other characteristics. An exemplary device actuation sequence is shown in FIGS. 11-13 for dispensing the disclosed dosage forms comprises a mechanical component or assembly 193 for compressing the propellant well to increase the internal pressure and a mechanical component or assembly 192 for compressing the dispensing well, crushing it, at least partway and forcing the piercing tip of the piercing device through the piercing surface of the dispensing chamber 106.

Additionally, the dispenser may employ a dispense actuator FIG. 14, 225 that receives a physical input from the user to trigger the dispense. Embodiments presently disclosed include mechanical means of actuating the dispense FIGS. 15-16 which transfer force input from the hand of the user through an actuating device that then drives the compression of each of the propellant 231 and dispensing chambers 232 in a mechanically timed sequence. However, it is contemplated that the mechanical input of the user could be translated into stored energy to be released using actuation of a release mechanism, or that the actuation can be automated through other methods (e.g.—electromechanical, pneumatic) wherein the user input is the press of a button to cause the automated action or sequence of actions.

However, it is contemplated that under certain conditions it could be advantageous to compress the propellant chamber only partway prior to beginning the dispensing chamber compression FIG. 16, or that under certain other conditions it could be advantageous to compress the dispense chamber prior to initiating compression of the propellant chamber. Numerous methods for creating a specific mechanical sequence of events from a single user action can be utilized. One embodiment includes a linear cam FIG. 14, 225 (also shown in FIGS. 15-16). Sliding the linear cam surfaces from their initial positions to their final positions causes cam following features 221, 223 on each of the compressing components to compress the blister wells.

Through experimentation it was determined that using serrations in the cam surface 225 compressing component to impart vibration into the dispense chamber aids the deaggregation and entrainment of powder in the gas propellant during dispensing. The serrations in the cam are designed to induce a vibration that produced between 5-50 cycles over the course of the crush of the dispensing blister. The use of serrations on the dispense chamber compression component can produce a higher percentage of mass dispensed as well as a particle size distribution with fewer clumped particles as measured by a laser defractometer versus an equivalent dispense chamber compression component without serrations. The serrations are designed so that the vibrations induced begin to occur as the powder blister crush is initiated continuing until just after the dispense chamber has been punctured. The initiation of the vibration prior to puncture allows for the particles to begin to deaggregate prior to the airflow initiation created by the puncture and release of air which helps to reduce the particle size distribution. The continuation of the vibration for a period of time after the puncture helps to improve the dose delivered by assisting the entrainment of the powder for powder particles that otherwise might have remained adhered to a surface inside the chamber.

In other embodiments of the dispenser the vibrations can be imparted on the dispense chamber or powder containing chamber through serrations on the linear cam which impart vibration through the dispenser or dispense chamber compression component. In other embodiments the dispenser may contain an electronic means of vibration such as a weighted electric motor vibrator or a piezo electric vibrator or other suitable devices.

FIG. 17 discloses an additional embodiment whereby the propellant and dispensing forms 231, 232 may be positioned orthogonally and may include sequential expression by a single mechanism. Such or similar configuration may provide more compact device design, simplification of use, or other advantages and numerous other mechanical arrangements are contemplated herein.

The invention claimed is:

1. A dry powder unit dose device, comprising:

a dosage form comprising more than one blister well;

wherein a blister well contains an internal piercing device and a dry powder, and at least one additional-blister well contains a gas propellant;

wherein the at least one propellant containing blister well is in fluid communication with said powder containing blister well upon rupture of a frangible sealed interface between the propellant containing blister well and the powder containing blister well;

wherein the internal piercing device further comprises a base and an elongated piercing member wherein the elongated piercing member further comprises a flow directing channel oriented axially upon the base such that it is substantially opposite an inflow of propellant; and wherein the flow directing channel of the internal piercing device is horizontally positioned on the base substantially off center and substantially opposite an end of the blister well where propellant flows into the powder containing blister well during dispense.

2. The dry powder unit dose device of claim 1, wherein the frangible sealed interface between the gas and powder containing blister wells further comprises an elongated path channel.

3. The dry powder unit dose device of claim 1 wherein the gas propellant is nitrogen.

4. A delivery system for administering a dry powder substance to a subject, comprising:

a handheld dispensing device;

a dosage form comprising more than one blister well;

wherein a blister well contains an internal piercing device and a dry powder, and at least one additional blister well contains a gas propellant;

wherein the at least one propellant containing blister well is in fluid communication with said powder containing blister well upon rupture of a sealed interface between the propellant containing blister well and the powder containing blister well; and wherein the internal piercing device further comprises a base and an elongated piercing member wherein the elongated piercing member further comprises a flow directing channel oriented axially upon the base such that it is substantially opposite an inflow of propellant and is horizontally positioned on the base substantially off center and substantially opposite an end of the blister well where propellant flows into the powder containing blister well during dispense.

5. The delivery system of claim 4, wherein the sealed interface between the gas and powder containing blister wells of the dosage form further comprises an elongated path channel.

6. The delivery system of claim 4, wherein the dosage form further comprises a pinching mechanism configured to provide the sealed interface between the gas and powder containing blister wells.

7. The delivery system according to claim 4, wherein the gas propellant is nitrogen.

8. The delivery system of claim 4, wherein the handheld dispensing device further comprises an actuator mechanism configured to sequentially time the compression of the blister wells.

9. The delivery system of claim 8, wherein the dispensing device actuator mechanism further comprises an electromechanical device.

10. The delivery system of claim 4, wherein the dispensing device further comprises a serrated surface upon a device component.

11. The delivery system of claim 1, wherein the dosage form further comprises a pinching mechanism configured to provide the sealed interface between the gas and powder containing blister wells.

12. A dry powder unit dose device, comprising:
a dosage form comprising more than one blister well;
wherein a first blister well contains an internal piercing device, a second blister well contains a dry powder, and at least one additional-blister well contains a gas propellant;
wherein the at least one propellant containing blister well is in fluid communication with said powder containing blister well upon rupture of a sealed interface between the propellant containing blister well and the powder containing blister well;
wherein the internal piercing device further comprises a base and an elongated piercing member wherein the elongated piercing member further comprises a flow directing channel oriented axially upon the base such that it is substantially opposite an inflow of propellant; and
wherein the flow directing channel of the internal piercing device is horizontally positioned on the base substantially off center and substantially opposite an end of the first blister well.

\* \* \* \* \*